United States Patent
Butnor et al.

(10) Patent No.: US 6,692,970 B2
(45) Date of Patent: Feb. 17, 2004

(54) AUTOMATED CARBON EFFLUX SYSTEM

(75) Inventors: John R. Butnor, Durham, NC (US); Christopher A. Maier, Hurdle Mills, NC (US); Kurt H. Johnsen, Durham, NC (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 200 days.

(21) Appl. No.: 09/755,361

(22) Filed: Jan. 5, 2001

(65) Prior Publication Data

US 2002/0000226 A1 Jan. 3, 2002

Related U.S. Application Data

(60) Provisional application No. 60/177,340, filed on Jan. 19, 2000.

(51) Int. Cl.[7] .......................... G01N 7/00; G01N 33/24; G01N 33/00
(52) U.S. Cl. .................. 436/148; 436/32; 436/127; 436/133; 422/82.13; 422/83
(58) Field of Search ................ 422/82.13, 83; 436/148, 25, 139, 141, 133, 32, 127; 73/19.05, 23.2, 864.81, 864.83; 166/250, 254

(56) References Cited

U.S. PATENT DOCUMENTS

| | | | |
|---|---|---|---|
| 4,816,412 A | 3/1989 | Schmidt et al. | 436/33 |
| 5,271,900 A | 12/1993 | Morita | 422/80 |
| 5,332,901 A | 7/1994 | Eckles et al. | 250/345 |
| 5,340,987 A | 8/1994 | Eckles et al. | 250/345 |
| 5,355,739 A | 10/1994 | Cooper et al. | 73/864 |
| 5,457,320 A | 10/1995 | Eckles et al. | 250/345 |
| 5,887,547 A | 3/1999 | Caveny et al. | 119/174 |
| 5,975,020 A | 11/1999 | Caveny et al. | 119/174 |

OTHER PUBLICATIONS

Eklund, "Practical Guidance for Flux Chamber Measurements of Fugitive Volatile Organic Emission Rates", J. Air Waste Manage. Assoc., 1992, v. 42, pp. 1583–1591.*

* cited by examiner

*Primary Examiner*—Jill Warden
*Assistant Examiner*—Yelena Gakh
(74) *Attorney, Agent, or Firm*—John D. Fado; Janet I. Stockhausen

(57) ABSTRACT

A method and apparatus are provided for measuring the gas efflux from a substrate. In particular, one or more measuring chambers receive a gas enriched air from the substrate. A respiration system sends reference air having a known gas concentration to the measuring chamber. The reference air mixes with the gas enriched air to form a mixed air, which is returned to the respiration system. The respiration system then measures the gas efflux of the substrate over the given amount of time.

18 Claims, 2 Drawing Sheets

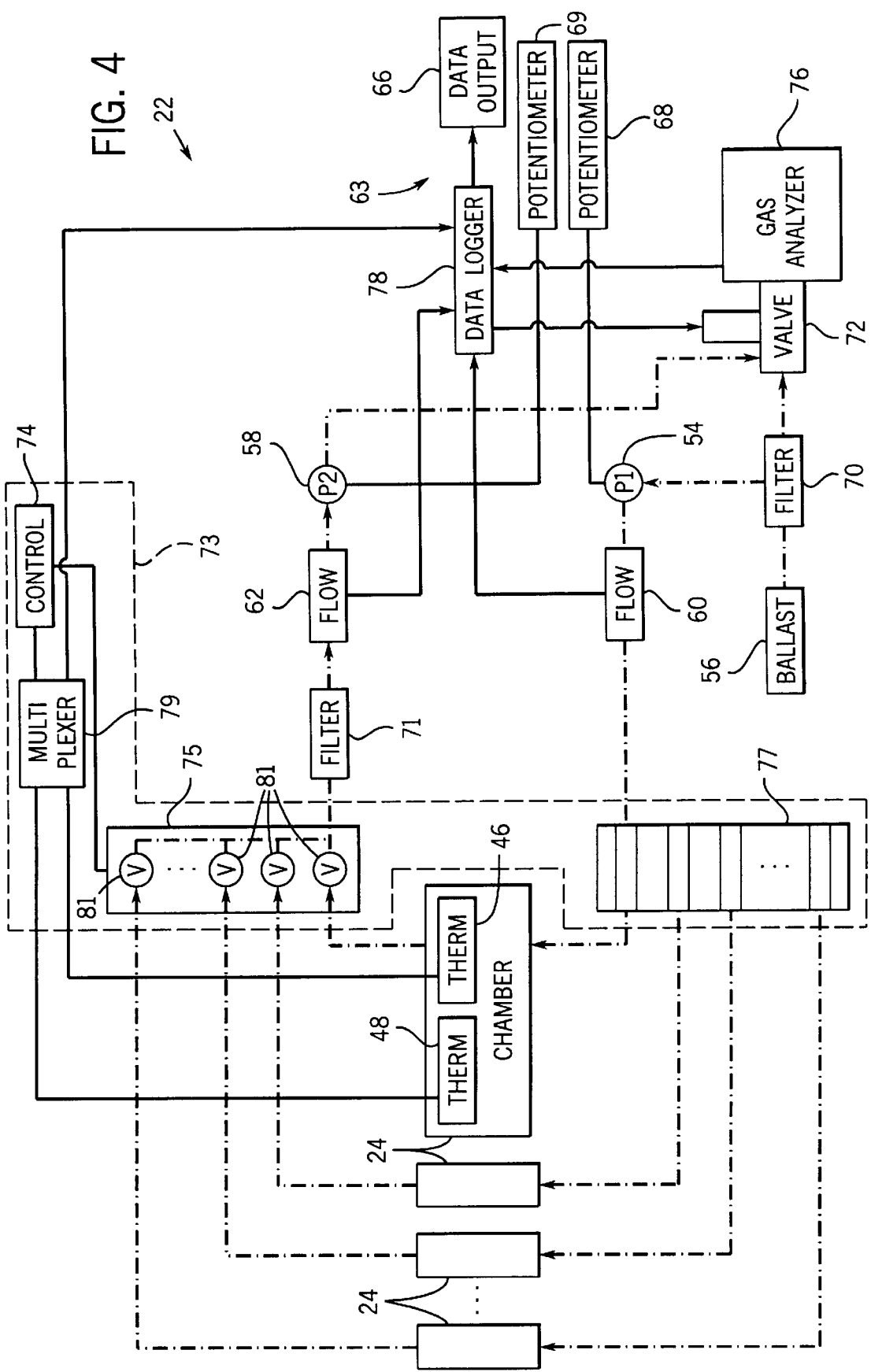

AUTOMATED CARBON EFFLUX SYSTEM

CROSS-REFERENCE TO RELATED APPLICATIONS

This application is based on provisional application No. 60/177,340 filed Jan. 19, 2000, and claims the benefit thereof. Ser. No. 60/177,340 is incorporated by reference herein.

STATEMENT REGARDING FEDERALLY SPONSORED RESEARCH OR DEVELOPMENT

BACKGROUND OF THE INVENTION

Terrestrial ecosystems serve as significant sources and sinks for various gases, such as carbon dioxide ($CO_2$). In natural forest ecosystems, $CO_2$ is generally absorbed through the forest canopy as photosynthesis occurs and emitted back into the atmosphere through the respiration of living organisms, with as much as 50% or more being emitted by decay bacteria and fungi as they decompose tissues in the forest soil. Tree roots, living woody tissue as well as night-time respiration of foliage also contribute to the efflux of $CO_2$ from forest systems. As the forest matures and its canopy grows, the level of carbon influx may exceed the level of carbon efflux. Forests typically move from being sources of atmospheric carbon after a disturbance that removes the canopy, i.e. forest operations or fire, to a sink of carbon at some later stage of maturity. We are now in an age where carbon pool management is being politicized and legislated while the role soil respiration (combination of respiration of soil microbes and living roots) plays in carbon budgets continues to be refined. This is of particular interest in both agricultural systems and managed forest ecosystems, where management/cultural decisions may have a substantial impact on the net carbon balance. Cultural practices, site preparation, nutritional amendments and genetic improvement all have the potential to influence net ecosystem productivity and affect carbon sequestration.

The measurement of soil, woody debris, root and stem respiration is essential to understanding the loss of carbon in the ecosystem. Early sampling techniques measured carbon loss using closed, static chambers placed on the soil surface and the rate of $CO_2$ accumulation was assessed by measuring the amount of $CO_2$ captured in an alkali trap (KOH, NaOH, or Soda Lime) over a fixed period of time. Other alternative static methods require the periodic drawing of samples from the soil so as to measure its carbon concentration with gas chromatography and compute its carbon flux rate over the collection period.

These static methods, however, suffer from several drawbacks. For instance, they are exceptionally burdensome to technicians taking diurnal carbon efflux measures, who are required to manually perform each measurement individually, in single chambers. Additionally, the accumulation of high concentrations of $CO_2$ in the collection chambers results in a greater storage of $CO_2$ in the soil, which changes the soil's $CO_2$ diffusion paths, and results in a reduction in the soil's respiration rate over time. These limitations hinder the studying of $CO_2$ efflux changes in dynamic terrestrial ecosystems.

What is therefore needed is a better system which provides for the accurate, continuous measurement of soil and woody tissue respiration rates as they fluctuate diurnally and seasonally.

BRIEF SUMMARY OF THE INVENTION

In accordance with a first aspect of the invention, an apparatus for measuring the efflux of gas from a substrate includes an inspection system having at least one air pump and a data analysis system. At least one measuring chamber has a substrate disposed therein that produces a quantity or a gas. A conduit system is attached to the measuring chamber at one end and to the inspection system at a second end. The at least one air pump supplies reference air having a known quantity of the gas to the at least one chamber via the conduit system so as to mix the reference air with the gas to produce a mixed air. The mixed air is then sent to the inspection system via the conduit system, and the data analysis system is able to measure the unknown quantity of gas.

These as well as other features and characteristics of the present invention will be apparent from the description which follows. In the detailed description below, preferred embodiments of the invention will be described with reference to the accompanying drawings. These embodiments do not represent the full scope of the invention. Rather the invention may be employed in other embodiments. Reference should therefore be made to the claims herein for interpreting the breadth of the invention.

BRIEF DESCRIPTION OF THE DRAWINGS

Reference is hereby made to the following figures in which like reference numerals correspond to the like parts throughout and in which:

FIG. 4 is a schematic illustration of the gas efflux measuring assembly in accordance with the preferred embodiment.

DETAILED DESCRIPTION OF THE INVENTION

Figure 1:
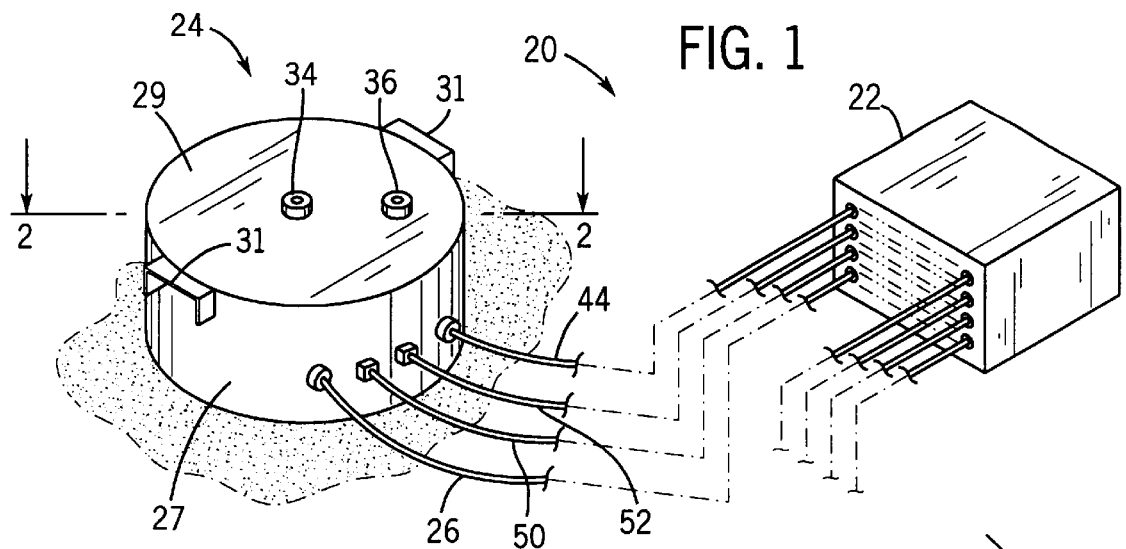
FIG. 1 is an illustration of a gas efflux measuring assembly constructed in accordance with a preferred embodiment of the invention.

Referring initially to FIG. 1, a gas efflux measuring assembly 20 includes one or more measuring chambers 24 that are each independently connected to a central inspection system 22 via hosing 26 and 44. Up to sixteen measuring chambers maybe supported by the inspection system 22 in accordance with the preferred embodiment, as will become apparent from the description below. Accordingly, while the preferred embodiment will be described as having sixteen measuring chambers 24, it should be appreciated that the invention is not to be construed as being limited to this configuration.

Each measuring chamber 24 comprises a generally cylindrical body 27 having an upper surface 29 and an open bottom 30. Disposed at the bottom of the cylindrical wall 27 is a metal lip or blade 32 that is configured to penetrate into the soil approximately 2 cm to form a quality seal with the soil surface to form an enclosed cavity defined by the soil, cylindrical wall 27, and upper surface 29. A pair of handles 31 is mounted onto wall 27 so that the chamber 24 is easily removable from the soil and transportable. At least one, and possibly two, vents 34 and 36 extend through the upper surface 29 and operate as pressure equilibration ports to promote an open flow through the chamber 24, as will be described below.

Accordingly, when the measurement chamber 24 is inserted into the soil, $CO_2$ that is produced by the soil disposed within the confines of the chamber will create a $CO_2$ enriched air therein. As will be described in more detail below, the inspection system 22 supplies a quantity of reference air, having a known $CO_2$ concentration, to the chamber 24. The reference air becomes mixed with the $CO_2$ enriched air to produce a mixed gas, which is transported from the chamber 24 to the central inspection system 22 for analysis.

Figure 2:
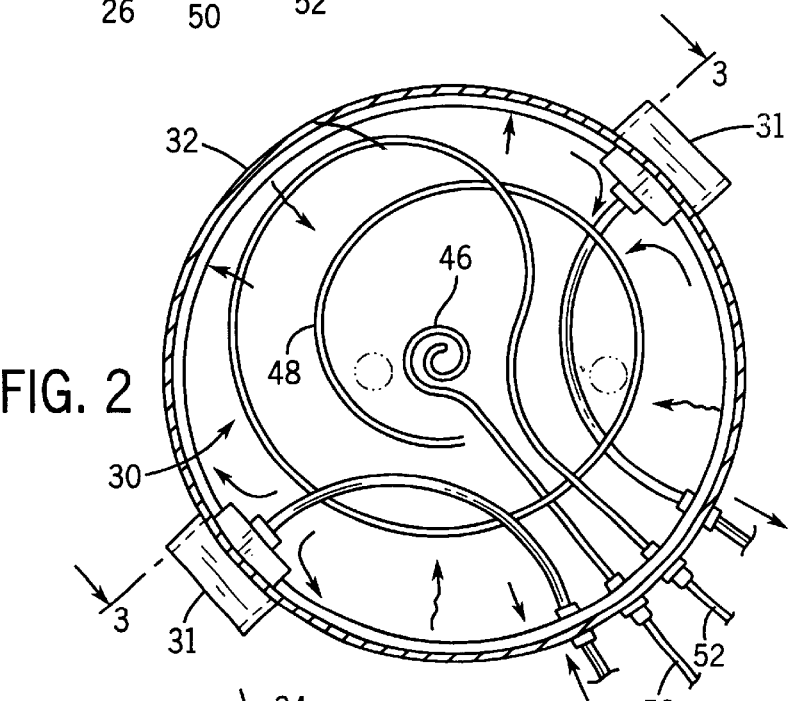
FIG. 2 is a top plan view of a measuring chamber of FIG. 1 taken along line 2—2.
Figure 3:
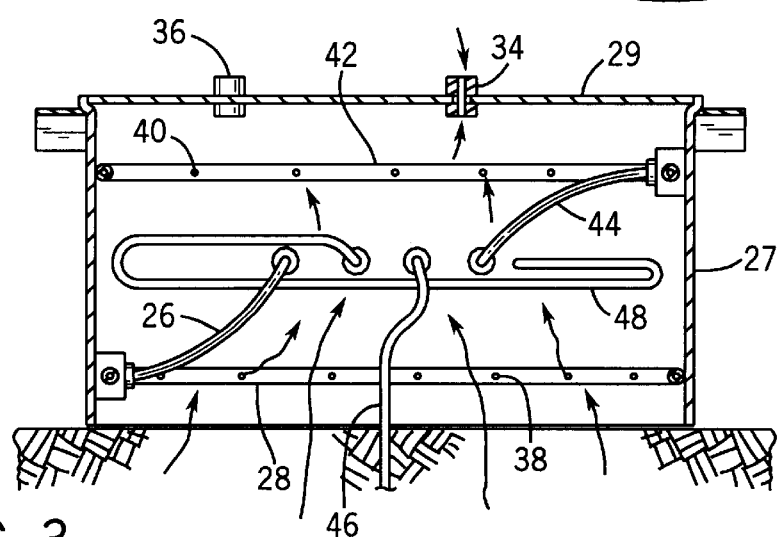
FIG. 3 is a sectional side elevation view of the measuring chamber of FIG. 2 taken along line 3—3.

Referring now to FIGS. 2 and 3, each measuring chamber 24 includes a lower and upper diffuser 28 and 42, respectively, that are mounted onto the inner surface of wall 27. The diffusers 28 and 42 are annular members that extend along the inner surface of wall 27, having holes 38 and 40 interspersed throughout and spaced widely apart at locations proximal hose 26. The holes 38 of the lower diffuser are more closely spaced as the distance from the hose 26 increases so that the reference air becomes evenly distributed throughout the diffuser 28. This ensures that the mixed air is uniform to improve the results of the subsequent analysis without the need to install a mixing fan in the chamber 24.

The lower diffuser 28 receives the reference air from the inspection system 22 via a supply tube 26. As will be described in more detail below, the reference air has a known $CO_2$ content that is used, in part, to determine the $CO_2$ efflux of the substrate. The mixed air then travels upwards through the chamber 24 into the upper diffuser 42, and is returned to the inspection system 22 via tubing 44 for analysis, as will be described in more detail below.

It should be appreciated that the fit between tubes 26 and 44 and the wall 27 is sealed to prevent the gas from escaping out the chamber 24. Furthermore, the measuring chambers 24 and hosing are generally constructed of non-porous material and may be designed in any manner capable of providing accurate measurements. For example, the tubing may be either ¼ or ⅜ inch Bevaline IV® tubing (registered trademark of Thermoplastic Processes Inc.) and supplied by Cole Parker Instrument Co., Vernon Hills, Ill. in accordance with the preferred embodiment. It should be appreciated in this regard that other types of tubing could be used having sufficient $CO_2$ properties, and a suitable crush resistance.

The measuring chamber 24 further includes a pair of thermocouples 46 and 48 that are operable to output the temperature of the soil and the mixed air inside the chamber 24, respectively. The thermocouples 46 and 48 are connected to a data logger 78 within the inspection system 22 via wires 50 and 51. The temperature information provided by the thermocouples increases the accuracy of the soil respiration analysis, and may be used to inform a user whether a given chamber positioned in direct sunlight, is overheating. As a further measure to protect against overheating, the outer surface of the measuring chamber 24 may include reflective insulation that prevents "greenhouse" heating. The chamber 24 may further be equipped with a soil moisture reflectometer, such as the type commercially available from Campbell Scientific Inc. 815 West, 1800 North, Logan Utah, (not shown) which takes soil moisture readings and can be installed in a common location for continuous measurement.

Referring now to FIG. 4, the inspection system 22 may be constructed from any suitably sized commercially available toolbox whose size is sufficient to accommodate the components, as will now be described. In particular, inspection system 22 includes an intake system including a filter 71, flow meter 62, and intake pump 58 that delivers mixed air from the chamber 24 to a gas analyzer via a solenoid valve 72, as will be described in more detail below. The inspection system 22 further includes an outtake system including a flow meter 60 and an outtake pump 54 that is configured to deliver reference air to the chamber 24, as will be described in more detail below. The pumps 54 and 58 used in accordance with the preferred embodiment are manufactured by Brailsford and Co. Inc, Rye, N.Y., such as the TD-4 NL(1), and operate under 12 volts of power (power supply not shown). The mass flow meters 60 and 62 used in accordance with the preferred embodiment are manufactured by Sierra Instruments Inc, Monterey Calif. and sold as the Top Track model 822.

The pumps are capable of producing flow rates of up to 3.0 liters per minute in accordance with the preferred embodiment. The flow generated by pumps 54 and 58 is controlled manually, for example, by potentiometers 68 and 69, and is controlled such that the outtake flow rate is slightly greater than the intake flow rate. These flow rates maintain a slight positive pressure within the chamber 24, as will be described in more detail below.

The inspection system 22 further includes a ballast tank 56 that is used in combination with the outtake system to provide a source of stable reference air, as the $CO_2$ concentration in ambient air can fluctuate widely, which would introduce noise into the respiration measurement. The ballast tank 56 is a relatively large plastic vessel having holes in its outer wall that are open to the ambient environment. The tank 56 also has a sufficient volume such that the ambient air becomes mixed therein to minimize the variability of $CO_2$ concentrations that may exist in the ambient environment. In accordance with the preferred embodiment, the tank 56 is formed from the Action Packer cargo box manufactured by Rubbermaid, Inc, Wooster, Ohio, and has a volume of approximately 132 liters. In extreme circumstances, where the $CO_2$ concentration is fluctuating too rapidly to be overcome using the ballast tank 56, an air compressor (not shown) could be used instead of the ballast tank 56 to homogenize the $CO_2$ concentration. In accordance with the preferred embodiment, the reference air flows from the ballast tank 56, through a filter 70, and to the outtake pump 54.

The inspection system 22 further includes a gas analysis system 63 including the gas analyzer 76, data logger 78, and a data output terminal 66. The gas analyzer 76 is operable to determine the $CO_2$ concentration of the mixed gas, and to output the results to the data logger 78, which additionally receives temperature and flow data from thermocouples 46 and 48 and flow meters 58 and 60, respectively. The data logger 78 then calculates the gas efflux, as well as the temperatures from thermocouples 46 and 48. The data output terminal 66 receives data from the data logger 78, and displays data to the user regarding the gas efflux of the substrate over a given period of time, the temperature of the soil and air within a given chamber, as well as any additional desirable parameters. It should be easily appreciated that the preferred embodiment could be configured to measure the respiration of any suitable substrate that is disposed within a chamber.

Operation of the assembly will now be described with reference to the measuring of carbon efflux of a substrate, such as soil, disposed in one of the chambers 24, though it should be appreciated that the present invention is capable of systematically analyzing substrates in a plurality of chambers, as will be described in more detail below. The reference air travels from the ballast tank 56, through a filter 70, and to a solenoid valve 72. The solenoid valve 72 used in accordance with the preferred embodiment is the type manufactured by Versa Products Co. Inc., 22 Spring Valley Road, Paramus, N.J. The valve 72 is controlled by data logger 78, and couples the reference air to the gas analyzer 76. As will be described in more detail below, the valve 72 also receives the mixed air as input, and iteratively allows the mixed air and reference air to be analyzed by the gas analyzer 76, as will be described in more detail below.

As described above, the reference air additionally flows from the ballast tank 56 to an outtake pump 54, and from the pump to the lower diffuser 28 via the mass flow meter 60. Analog output of the outtake flow is sent from the mass flow meter 60 to the datalogger 78 for use during the carbon efflux analysis, as will be described in more detail below. Once the reference air becomes mixed with the $CO_2$ enriched air in the chamber 24 to form the mixed air that is to be analyzed, the mixed air flows upwardly in the measuring chamber 24 towards the upper diffuser 42. Most of the mixed air enters the holes 40 in upper diffuser 42 under pressure supplied by the intake pump 58 via hosing 44. In particular, the intake pump 58 supplies suction within the chamber 24 which causes the mixed air to flow upwards and into the upper diffuser 42.

The remaining mixed air that does not enter the diffuser 42 exits the chamber 24 via the equilibration ports 34 and 36 to produce an open flow-through design. Accordingly, the equilibration ports 34 and 36 ensure that the air pressure within the measuring chamber 24 is near ambient and that any leaks are pushing outwards to prevent ambient air having an unknown $CO_2$ concentration from entering the chamber 24. The flow of the outtake pump 54 is therefore adjusted so as to provide a greater flow rate than that of the intake pump 58 so as to ensure that the mixed air rises within the chamber 24. As a result, in order to maintain accurate gas and data measurements, the overall air flow entering the measuring chamber is greater than the overall air flow exiting the chamber, thus providing a slightly positive chamber pressure of preferably no greater than 0.5 Pa, as pressures greater than this amount have been empirically found to adversely affect the reliability of the soil respiration analysis.

In addition, the constant airflow through the chamber 24 ensures that the air will remain at equilibrium, avoiding the accumulation of $CO_2$ enriched air during non-sampling periods. This will facilitate more rapid measurements when as the system will not have to wait for the air inside a given chamber 24 to reach equilibrium when the air inside that chamber is to be analyzed. Furthermore, it has been determined that excess $CO_2$ inhibits soil respiration and, accordingly, the equilibration ports 34 and 36 and open flow-through design facilitate soil respiration to improve the accuracy of the measurements. Additionally, it has been observed that the humid air emitted by the soil can produce condensation that could obstruct air from entering the return tube 44. The constant influx of reference air removes the more humid air, and additionally removes excess moisture from the tubing. It is therefore advantageous to supply reference air to the chamber 24 even when that chamber is not being analyzed, as will be described in more detail below. Equilibration port 36 may further be connected to a digital manometer (not shown) to verify pressure differential between the chamber and the outside environment.

The mixed air flows from tubing 44 into a filter 71, through a flow meter 42 and intake pump 58, and into the valve 72. To measure the carbon efflux of the substrate in one of the chambers 24, the $CO_2$ concentration in the reference air as well as the $CO_2$ concentration in the mixed air is measured by the single cell gas analyzer 76, such as the type commercially available from PP Systems, located at Unit 2, Glovers Court, Bury Mead Road, Hitchin, Herts, SG5 1RT UK. It should be appreciated, however, that the gas analyzer 76 may alternatively comprise any suitable gas analyzer. For example, a differential gas analyzer could be used that would directly accept the two inputs, thereby foregoing with the implementation of the two-way solenoid pinch valve 72. In accordance with the preferred embodiment, the valve 72 iterates under the control of data logger 78 from a first position that allows reference air to flow into the gas analyzer 76 while shunting away the gas enriched air, to a second position that allows the gas enriched air to be analyzed while shunting away the reference air.

The gas analyzer 76 then determines the gas concentration of the air being analyzed, and communicates the results to the data logger 78, which comprises Model Number CR 23 X commercially available from Campbell Scientific.

The data logger 78 calculates the gas efflux by first determining the molar flow rate of air passing through the measuring chamber (AFlow). Next, the flux rate of the gas (Flux) is determined based on the difference in $CO_2$ values between the reference air and the mixed air. Finally, the gas efflux value is that flux expressed over the area of the substrate measured.

The flow rate of the air passing through the chamber 24 is expressed by the equation:

$$AFlow (\text{moll min}) = \frac{Flow(\text{lpm})}{22.4} * \frac{273.15}{273.15 + air\ temp} + \frac{BP(\text{kPa})}{101.3} \quad (1)$$

The flow is divided by 22.4 as 22.4 is the volume of 1 mole of air (dm3) at S.T.P. The air temp is the temperature (Celsius) of the air in chamber 24. BP(kPa) is the barometric pressure in kilopascals.

The flux rate of the gas is then determined by the equation:

$$Flux(\mu mol/s) = \frac{(\Delta CO_2 * AFlow)}{60} \quad (2)$$

In equation 2, $\Delta CO_2$ is the difference in $CO_2$ concentration between the reference air and the mixed air, as determined by the gas analyzer 76 and data logger 78.

The carbon efflux, or soil respiration, is the flux expressed over the area of substrate measured, as determined by the equation:

$$Respiration\left(\frac{\mu mol}{s^{-1} m^{-2}}\right) = \frac{Flux}{surface\ area} \quad (3)$$

As described above, the inspection system 22 is capable of determining the carbon efflux of substrates disposed in a plurality of chambers, and up to 16 chambers in accordance with the preferred embodiment. In accordance with this embodiment, the invention employs a multiport system 73 supporting the series of measuring chambers whose gas efflux is measured sequentially (fixed or variable time step) using the gas analyzer 76. In particular, the outtake pump 54 of the inspection system 22 is connected to a first manifold 75 having a number of two-way solenoid valves 81 disposed therein that are, in turn, connected to the mixed flow hosing 44 of a corresponding number of chambers chamber 24. The valves are operated by a control 74 such that only one of the valve is open at a time, thereby ensuring that the mixed flow from only one chamber is measured by the gas analyzer 76 at any given time. As described above, the valve 72 connected to the gas analyzer 76 iterates between a first position, allowing the reference air to be sampled, and a second position whereby the mixed air is output to the gas analyzer 76.

The outtake pump 54 of the inspection system 22 sends the reference air through a second manifold 77 having a conduit system corresponding to each chamber such that a constant supply of reference air is supplied to each chamber via hosing 26. Accordingly, during non-sampling periods, each measuring chambers 24 is continuously flushed with reference air to prevent gas efflux accumulation within the chamber, as described above. As during sampling periods, the reference air is continuously supplied to the measuring chamber 24 along the first air hose 26 and allowed to mix with the gas efflux to form the gas enriched air. When that chamber 24 is not being sampled, the mixed air, instead of being pulled into the inspection system 22 via hosing 44, exits through the equilibration ports 34 and 36. This one-way pumping of reference air is usually performed at 1.50 liters per minute, per chamber, resulting in a positive pressure of preferably no greater than 0.5 Pa within the chamber, as discussed above.

Additionally, when a plurality of measuring chambers 24 are connected to the inspection system 22, the corresponding thermocouples 46 and 48 for each chamber output to a multiplexer 79, which operates under commands from control 74. The multiplexer 79 outputs data to the data logger 78, which provides measurements of the soil and air temperature in each chamber 24.

This embodiment may also take advantage of a null chamber (not shown) to assist in the determination of carbon efflux. In particular, the null chamber is similar to the measuring chamber 24, except the bottom 30 which is normally in contact with the soil is sealed to form an enclosed cavity, having ventilation ports 34 and 36. Reference air is supplied and sampled as described above. The sampling of the null chamber will produce a slightly positive or slightly negative carbon efflux value, which accounts for minor variations of the reference air and any absorption or desorption of CO2 by system components. Accordingly, the efflux value obtained from the null chamber may be added to the value obtained for each measuring chamber 24 to provide a more accurate calculation of the carbon efflux.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements included within the spirit and scope of the invention, as set forth by the appended claims.

We claim:

1. An apparatus for measuring gas efflux from a substrate comprising:
    an inspection system having at least one air pump and a data analysis system;
    at least one measuring chamber having a substrate disposed therein said substrate producing an unknown quantity of gas;
    a conduit system attached to said at least one measuring chamber at one end and to the data analysis system of said inspection system at a second end, wherein said at least one air pump supplies reference air from a ballast tank through said conduit system to the at least one measuring chamber and mixed air is returned to the data analysis system of said inspection system through said conduit system; and
    wherein the at least one air pump supplies reference air having a known quantity of the gas to the at least one measuring chamber via the conduit system so as to mix the reference air with the gas to produce a mixed air, and wherein the mixed air is sent to the inspection system via the conduit system, and wherein the data analysis system is configured to measure the unknown quantity of gas, and wherein a positive measuring chamber pressure of no greater than 0.5 Pa is maintained.

2. The apparatus as recited in claim 1, wherein the conduit system further comprises a supply tube and a return tube, wherein the supply tube supplies the reference air to the at least one measuring chamber, and wherein the return tube receives the mixed air from the at least one measuring chamber.

3. The apparatus as recited in claim 2, wherein the at least one measuring chamber includes a first diffuser having a plurality of apertures, wherein the at least one measuring chamber is in fluid communication with the supply tube through said first diffuser which is attached to said supply tube and reference air is supplied to the at least one measuring chamber through said first diffuser.

4. The apparatus as recited in claim 3, wherein the at least one mixing chamber includes a second diffuser having a plurality of apertures, wherein the at least one measuring chamber is in fluid communication with the return tube through said second diffuser which is attached to said return tube and mixed air from the at least one measuring chamber enters the return tube through the apertures of said second diffuser.

5. The apparatus as recited in claim 4, wherein the first and second diffusers comprise annular bodies.

6. The apparatus as recited in claim 1, wherein the at least one measuring chamber further includes an equilibration port configured to release air that is disposed within the at least one measuring chamber into the environment.

7. The apparatus as recited in claim 6, wherein air is supplied to the at least one measuring chamber at a greater flow rate than the rate at which the mixed air is sent to the inspection system.

8. The apparatus as recited in claim 6, wherein the at least one measuring chamber further comprises a second equilibration port configured to release air disposed within the at least one measuring chamber into the environment, wherein said second equilibration port is equipped with a pressure measuring device so as to determine the pressure of air released from the second equilibration port.

9. The apparatus as recited in claim 1, wherein the data analysis system comprises at least one flow meter, a gas analyzer, and a data output system, wherein the at least one flow meter measures the rate at which the reference air is supplied to the at least one measuring chamber and the rate at which the mixed air is sent from the at least one measuring chamber to the inspection system, and wherein the gas analyzer determines the gas concentration in the reference air and the mixed air, and wherein the data output system determines the unknown quantity of gas.

10. The apparatus as recited in claim 1, wherein the at least one measuring chamber further comprises a first thermocouple to measure the temperature of the substrate, and a second thermocouple to measure the temperature of the chamber.

11. The apparatus as recited in claim 1, further comprising a plurality or measuring chambers that are coupled to the inspection system, and wherein the inspection system iterates between said plurality of measuring chambers so as to measure unknown quantities of gas that are emitted by a plurality of substrates.

12. A method of measuring gas efflux from a substrate, comprising the steps of:
   (a) placing at least one measuring chamber in fluid communication with a inspection system;
   (b) accumulating a quantity of a gas from the substrate within the at least one measuring chamber over a predetermined amount of time;
   (c) sending reference air from the ballast tank to the inspection system into the at least one measuring chamber, wherein the reference air has a known quantity of the gas;
   (d) mixing the reference air with the gas from the substrate within the at least one measuring chamber to produce a mixed air;
   (e) sending the mixed air to the inspection system; and
   (f) measuring the quantity of the accumulated gas from the substrate inside the inspection system over the amount of time.

13. The method as recited in claim 12, further comprising between steps (e) and (f), measuring the quantity of the gas from the mixed air and subtracting the known quantity of gas from the reference air over the amount of time.

14. The method as recited in claim 13, further comprising sending the reference air at a greater rate than the mixed air.

15. The method as recited in claim 14, further comprising releasing a portion of the mixed air out the at least one measuring chamber through an equilibration port.

16. The method as recited in claim 15, further comprising releasing the portion of the mixed air through the equilibration port at a rate that is less than the difference between the rate of sending the reference air and sending the mixed air so as to maintain an air pressure within the at least one measuring chamber of no greater than 0.5 Pa.

17. The method as recited in claim 12, wherein step (a) further comprises placing a plurality of measuring chambers in fluid communication with the inspection system, and repeating steps (b) through (f) for each chamber.

18. A method for measuring the efflux of a gas from a substrate comprising the steps of:
   sealing at least one measuring chamber having an equilibration port, a first diffuser and a second diffuser, against an area of substrate having a gas efflux to be measured;
   with a first pump, pumping into the at least one measuring chamber through the first diffuser of each measuring chamber a continuous supply of a reference air from a ballast tank such that the reference air diffuses with the gas efflux to form a gas enriched air and with a second pump, pumping from the at least one measuring chamber through the second diffuser of each measuring chamber a continuous supply of the gas enriched air such that the amount of reference air entering the at least one measuring chamber is greater than the amount of gas enriched air exiting the at least one measuring chamber and a positive measuring chamber pressure of no greater than 0.5 Pa is maintained;
   continuously analyzing the gas enriched air withdrawn from the at least one measuring chamber over a period of time to collect a plurality of gas concentration measurements from the gas enriched air and to collect a molar flow rate measurement of the gas enriched air passing through the measuring chamber; and
   determining the gas efflux of the substrate according to the gas concentration measurements and the molar flow rate measurement.

* * * * *